United States Patent [19]

Los et al.

[11] 4,164,404
[45] Aug. 14, 1979

[54] DITHIINDICARBOXIMIDE, DITHIOLANEDICARBOXIMIDE, THIAPYRANDICARBOXIMIDE AND PYRANDICARBOXIMIDE DERIVATIVES AS PLANT GROWTH REGULANTS

[75] Inventors: Marinus Los; Bryant L. Walworth, both of Pennington, N.J.

[73] Assignee: American Cyanamid Company, Stamford, Conn.

[21] Appl. No.: 474,760

[22] Filed: May 30, 1974

Related U.S. Application Data

[63] Continuation-in-part of Ser. No. 373,556, Jun. 25, 1973, abandoned.

[51] Int. Cl.² ............... A01N 5/00; A01N 21/02; C07D 495/04; C07D 493/04; A01N 21/00
[52] U.S. Cl. ............... 71/77; 260/326.5 SA; 260/326.5 B; 260/326.28; 260/326.29; 71/76; 71/90; 71/91; 71/95; 549/15; 549/22
[58] Field of Search ............... 260/326.28, 326.29, 260/326.5 SA, 326.5 B, 326.5 SM, 325.5 B; 71/77, 90, 91, 95, 76

[56] References Cited

U.S. PATENT DOCUMENTS

| 3,123,618 | 3/1964 | Schumann et al. | 260/326.5 B |
| 3,549,655 | 12/1970 | Bublitz | 260/326.5 B |
| 3,790,597 | 2/1974 | Dexter et al. | 260/326.5 S |

FOREIGN PATENT DOCUMENTS

1815404  6/1970  Fed. Rep. of Germany ...... 260/326 N

*Primary Examiner*—Mark L. Berch
*Attorney, Agent, or Firm*—H. G. Jackson

[57] ABSTRACT

The invention is a novel class of dithiindicarboximido, dithiolanedicarboximido, thiapyrandicarboximido and pyrandicarboximido derivatives represented by the formula:

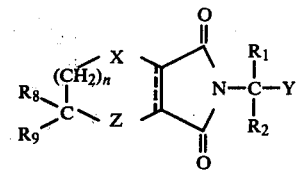

wherein X is $CH_2$ or S; Z is S, O or SO, provided that when Z is O, X cannot be S; Y is $-COOR_3$, $-CONR_4R_5$, $-CONHNR_6R_7$, $-CONHN^{\oplus}R_6R_7R_7 \cdot halide^{\ominus}$, CN, $-CONHOH$ or $-COR_{10}$; n is 0 or 1; $R_1$ and $R_2$ each represent alkyl $C_1-C_4$, or when taken together with the carbon to which they are attached form cycloalkyl $C_4-C_8$ or methyl-substituted cycloalkyl $C_4-C_9$; $R_3$ is hydrogen or alkyl $C_1-C_4$; $R_4$ and $R_5$ each represent hydrogen, alkyl $C_1-C_4$, phenyl, monohalophenyl, monoalkyl($C_1-C_4$)-phenyl or monoalkoxy($C_1-C_4$)phenyl; $R_6$ and $R_7$ are alkyl $C_1-C_2$; $R_8$ is hydrogen, alkyl $C_1-C_4$, phenyl, monohalophenyl, monoalkyl($C_1-C_4$)phenyl, monoalkoxy($C_1-C_4$)phenyl, mononitrophenyl or trifluoromethylphenyl; $R_9$ is hydrogen or alkyl $C_1-C_4$; $R_{10}$ is halogen; represents a single or double bond.

This invention also relates to a method for regulating the growth of plants with these compounds.

49 Claims, No Drawings

DITHIINDICARBOXIMIDE, DITHIOLANEDICARBOXIMIDE, THIAPYRANDICARBOXIMIDE AND PYRANDICARBOXIMIDE DERIVATIVES AS PLANT GROWTH REGULANTS

CROSS-REFERENCE TO RELATED APPLICATION

This application is a continuation-in-part application of U.S. Ser. No. 373,556, filed June 25, 1973, now abandoned.

BACKGROUND OF THE INVENTION

1. Field of the Invention:

The invention pertains to the chemical arts, i.e. dithiindicarboximide, dithiolanedicarboximide, thiapyrandicarboximide and pyrandicarboximide derivatives as plant growth regulants.

2. Description of the Prior Art:

Robert Eugene Diehl's and Bryant Leonidas Walworth's co-pending U.S. patent application, Ser. No. 348,355, filed Apr. 5, 1973 now abandoned which is a continuation-in-part of their co-pending Ser. No. 282,537 now abandoned, filed Aug. 21, 1972 discloses phthalimide derivatives as plant growth regulants.

SUMMARY OF THE INVENTION

The invention is novel compounds represented by the formula:

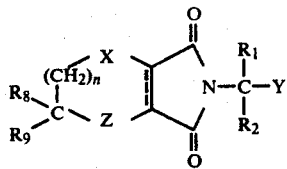

wherein X is $CH_2$ or S; Z is S, O or SO, provided that when Z is O, X cannot be S; Y is $-COOR_3$, $-CONR_4R_5$, $-CONHNR_6R_7$, $-CONHN^{\oplus}R_6R_7R_7\bullet halide^{\ominus}$, CN, $-CONHOH$ or $-COR_{10}$; n is 0 or 1; $R_1$ and $R_2$ each represent alkyl $C_1-C_4$, or when taken together with the carbon to which they are attached form cycloalkyl $C_4-C_8$ or methyl-substituted cycloalkyl $C_4-C_9$; $R_3$ is hydrogen or alkyl $C_1-C_4$; $R_4$ and $R_5$ each represent hydrogen, alkyl $C_1-C_4$, phenyl, monohalophenyl, monoalkyl($C_1-C_4$)-phenyl or monoalkoxy($C_1-C_4$)phenyl; $R_6$ and $R_7$ are alkyl $C_1-C_2$; $R_8$ is hydrogen, alkyl $C_1-C_4$, phenyl, monohalophenyl, monoalkyl($C_1-C_4$)phenyl, monoalkoxy($C_1-C_4$)phenyl, mononitrophenyl or trifluoromethylphenyl; $R_9$ is hydrogen or alkyl $C_1-C_4$; $R_{10}$ is halogen; and ═══ represents a single or double bond. These compounds are useful as plant growth regulating agents and as intermediates for the preparation of plant growth regulating agents. Compounds of the above structure, where Y is $-COR_{10}$ and $R_1$, $R_2$ and $R_{10}$ are as described, are primarily useful as intermediates for the preparation of the plant growth regulating agents. Similarly, compounds having the above formula, wherein Y is $-COOR_3$ and $R_3$ is hydrogen, are also primarily useful as intermediates.

DETAILED DESCRIPTION

In accordance with the invention, the above-identified dithiindicarboximide, dithiolanedicarboximide, thiapyrandicarboximide and pyrandicarboximide derivatives can be prepared by reacting the appropriate α-aminocarboxylic acid with the appropriate dithiindicarboxylic anhydride, dithiolanedicarboxylic anhydride, thiapyrandicarboxylic anhydride or pyrandicarboxylic anhydride, preferably in the presence of an aprotic solvent and a tertiary-amine, such as triethylamine. Among the solvents which are useful in carrying out this reaction are: benzene, toluene, xylene, dimethylformamide and acetic acid. In practice, it will be found that the reaction can be conducted at a temperature between about 80° C. and 225° C., and preferably between 120° C. and 150° C. Alternatively, the required product can be prepared by fusing the α-amino acid or acid derivative and the anhydride at temperatures between about 150° C. and 250° C., but preferably at 180° C. to 210° C. The reaction can be graphically illustrated as follows:

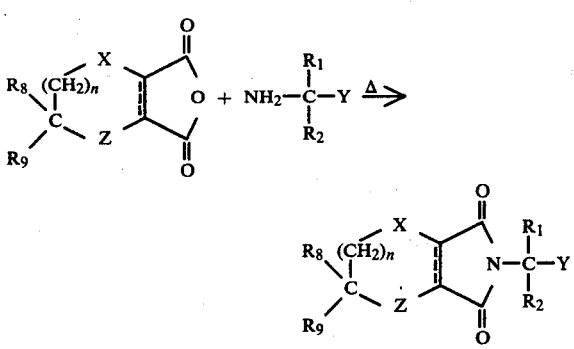

wherein X, Y, Z, n, $R_1$, $R_2$, $R_8$ and $R_9$ are as indicated above, with the exception that Y cannot be $-COR_{10}$ or $-CONHN^{\oplus}R_6R_7R_7\bullet halide^{\ominus}$.

In the case where Y is $-COOH$, the thus-formed acid can then be converted to the corresponding acid chloride or acid bromide by heating the acid with thionyl chloride, thionyl bromide, phosphorus pentachloride, or the like, preferably in the presence of an aprotic solvent, aromatic or chlorinated hydrocarbons such as benzene, xylene, toluene, methylene chloride, chloroform or dichloroethane. This reaction is graphically illustrated below, wherein thionyl halide, i.e. chloride or bromide, is representative of the halogenating agent employed.

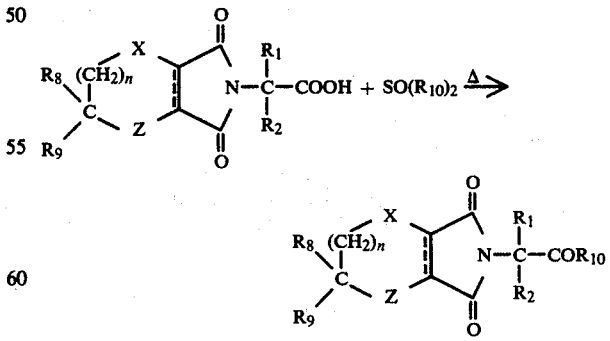

wherein X, Z, n, $R_1$, $R_2$, $R_8$, $R_9$ and $R_{10}$ are as described above.

The thus-formed acid chloride or acid bromide can then be converted to the corresponding amide or hydrazide by reaction thereof with ammonia, hydroxylamine, monoalkylamine, dialkylamine or dialkyl hydrazine, at a temperature between about −20° C. and +25° C., and preferably −10° C. to +15° C. This reaction is preferably carried out by dissolving the acid halide in a solvent such as acetone or a water-miscible ether such as tetrahydrofuran, dioxane, or the like, and bubbling ammonia gas through the thus-prepared solution while maintaining said solution in a stirred or agitated condition or by admixing the monoalkylamine, dialkylamine or dialkyl hydrazine with the thus-prepared solution. Alternatively, the amine, hydroxylamine or hydrazine can be dissolved in the solvent and then added to the acid halide in an aprotic solvent. The reaction can be graphically shown as follows:

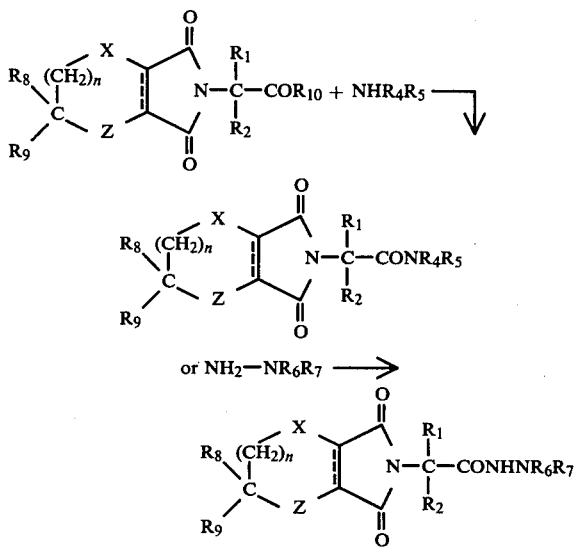

wherein X, Z, n, $R_1$, $R_2$, $R_4$, $R_5$, $R_6$, $R_7$, $R_8$ and $R_{10}$ are as defined above.

Alternatively, the dithiindicarboximido amides, dithiolanedicarboximido amides, thiapyrandicarboximido amides and pyrandicarboximido amides having the formula:

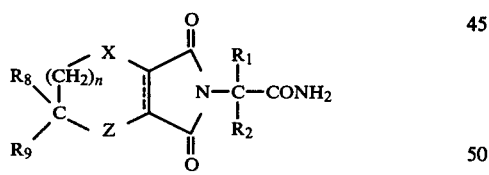

wherein X, Z, n, $R_1$, $R_2$, $R_8$ and $R_9$ are as described above, may be prepared by reacting the appropriate dithiindicarboxylic acid anhydride, dithiolanedicarboxylic acid anhydride, thiapyrandicarboxylic acid anhydride or pyrandicarboxylic acid anhydride with the appropriate α,α-disubstituted-α-aminonitrile to give the product:

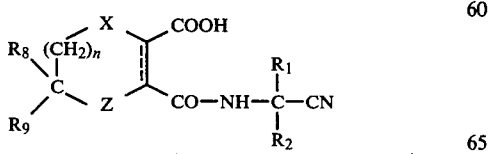

wherein X, Z, n, $R_1$, $R_2$, $R_8$ and $R_9$ are as defined above. This reaction is carried out at temperatures from about 20° C. to 60° C. in an inert solvent such as ether, tetrahydrofuran, chloroform, methylene chloride, benzene, toluene, acetonitrile, and the like. The thus-formed acid is then cyclized to the corresponding carboximide either thermally or by heating with a dehydrating agent such as acetic anhydride, acetyl chloride, thionyl chloride, or the like, at temperatures from about 0° C. to 100° C. The resulting product,

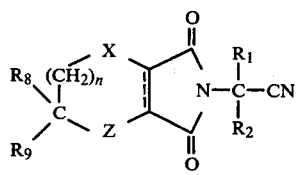

in which X, Z, n, $R_1$, $R_2$, $R_8$ and $R_9$ are as defined above, is converted to the active amide by hydration of the nitrile function. This reaction is preferably carried out with a strong acid such as sulfuric acid, preferably in the presence of a non-miscible solvent such as methylene chloride, chloroform, or the like, at temperatures from about −10° C. to +30° C.

Where a hydrazinium halide is desired, a hydrazide having the formula:

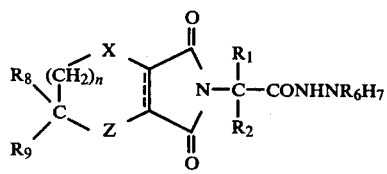

wherein X, Z, n, $R_1$, $R_2$, $R_6$, $R_7$, $R_8$ and $R_9$ are as defined above, can be treated with an alkyl halide in the presence of a solvent such as tetrahydrofuran, ether, dioxane, benzene, chloroform, or the like, at an elevated temperature to yield the desired corresponding hydrazinium halide.

To obtain the active dicarboximido ester represented by the formula:

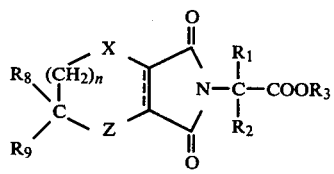

wherein X, Z, n, $R_1$, $R_2$, $R_8$ and $R_9$ are as defined above, and $R_3$ is alkyl $C_1$-$C_4$, the corresponding acid, i.e. where $R_3$ is hydrogen, is treated with a diazoalkane $C_1$-$C_4$ in the presence of a solvent such as an ether. This reaction can be carried out at a temperature between about −10° C. and +30° C.

Alternatively, the appropriate α-amine ester:

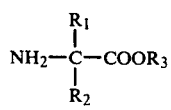

wherein $R_1$ and $R_2$ are as defined above and $R_3$ is alkyl $C_1$-$C_4$, can be allowed to react with the appropriate dicarboxylic anhydride:

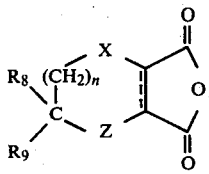

wherein X, Z, n, $R_8$ and $R_9$ are as defined above, to afford the corresponding ester:

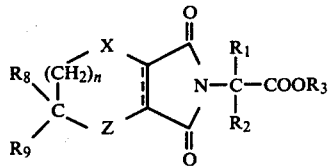

wherein $R_3$ is alkyl $C_1$-$C_4$ and X, Z, n, $R_1$, $R_2$, $R_8$ and $R_9$ are as previously defined. In yet another procedure, the acid halide, prepared as above, may be treated with a lower $C_1$-$C_4$ alkanol in the presence of an acid acceptor such as pyridine, triethylamine, sodium bicarbonate, and the like.

The dicarboximido nitrile:

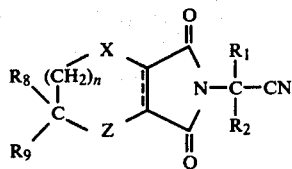

wherein $R_1$, $R_2$, $R_8$, $R_9$, X, Z and n are as described above, can be obtained by dehydration of the corresponding amide using titanium tetrachloride, acetic anhydride, phosphorus pentoxide, phosphorus oxychloride, or the like, in the presence of a solvent such as benzene, tetrahydrofuran, or the like. This reaction can be carried out at a temperature between about 0° C. and 100° C.

The plant growth regulating effects obtained with compounds having the structure:

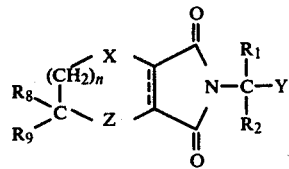

wherein X is $CH_2$ or S; Z is S, O or SO, provided that when Z is O, X cannot be S; Y is —$COOR_3$, —CONHOH, —$CONR_4R_5$, —$CONHNR_6R_7$, —CONHN⊕$R_6R_7R_7$•halide⊖ or CN; n is 0 or 1; $R_1$ and $R_2$ each represent alkyl $C_1$-$C_4$, or when taken together with the carbon to which they are attached form cycloalkyl $C_4$-$C_8$ or methyl-substituted cycloalkyl $C_4$-$C_9$; $R_3$ is alkyl $C_1$-$C_4$; $R_4$ and $R_5$ each represent hydrogen, alkyl $C_1$-$C_4$, phenyl, monohalophenyl, monoalkyl($C_1$-$C_4$)phenyl or monoalkoxy($C_1$-$C_4$)phenyl; $R_6$ and $R_7$ are alkyl $C_1$-$C_2$; $R_8$ is hydrogen, alkyl $C_1$-$C_4$, phenyl, monohalophenyl, monoalkyl($C_1$-$C_4$)phenyl, monoalkoxy($C_1$-$C_4$)phenyl, mononitrophenyl or trifluoromethylphenyl; $R_9$ is hydrogen or alkyl $C_1$-$C_4$; and $===$represents a single or double bond are most remarkable.

Preferred compounds of this invention are those represented by the above formula, wherein X and Z are each sulfur, and Y, n, $R_1$, $R_2$, $R_8$ and $R_9$ are as defined above; and particularly preferred compounds as those in which n is 1.

Another group of preferred compounds are those represented by the above formula, wherein X is $CH_2$; Z is oxygen; and n, Y, $R_1$, $R_2$, $R_8$ and $R_9$ are as described above.

A further group of preferred compounds are depicted by the above formula, wherein X is $CH_2$; Z is sulfur; and n, Y, $R_1$, $R_2$, $R_8$ and $R_9$ are as defined above.

A further group of preferred compounds are 5,6-dihydro-p-dithiin-2,3-dicarboximido derivatives represented by the formula:

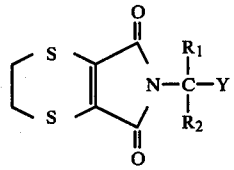

wherein Y is —$COOR_3$, —$CONR_4R_5$, —$CONHNR_6R_7$, —CONHN⊕$R_6R_7R_7$•halide⊖, CN, or —$COR_8$; $R_1$ and $R_2$ each represent alkyl $C_1$-$C_4$, or when taken together with the carbon to which they are attached form cycloalkyl $C_4$-$C_8$; $R_3$, $R_4$ and $R_5$ each represent hydrogen or alkyl $C_1$-$C_4$; $R_6$ and $R_7$ are alkyl $C_1$-$C_2$; and $R_8$ is halogen and a method for regulating the growth of plants with these compounds is a preferred method of the invention. These compounds and their use are disclosed and claimed in our copending parent application Ser. No. 373,556, filed June 25, 1973, now abandoned.

A still further group of preferred compounds are illustrated by the above formula, wherein X is S; Z is SO; and n, Y, $R_1$, $R_2$, $R_8$ and $R_9$ are as defined above.

A very surprising aspect of the invention is the finding that although the plant growth regulating effects of the compounds within the generic class described above sometimes varies from plant to plant and from compound to compound, said compounds are generally highly active at low rates of application and do not appear to be phytotoxic when applied at relatively high rates. In practice, it will generally be found desirable to employ from about 0.06 pound to 32 pounds per acre, and preferably 0.06 pound to 4.0 pounds per acre of the active dicarboximido compound in the treated area to obtain the desired plant growth regulant effect.

Among the desired effects obtained with the compounds of the invention are:

(A) Increased internode growth in certain crops evidenced by longer internodes having increased dry weight;

(B) Increased leaf size in certain crops evidenced by both increased leaf area and increased dry weight of leaves;

(C) Induced flowering and/or bolting in certain varieties of plants;

(D) Increased tuber set in tuberous plants;

(E) Increased height of certain seedling plants, and dwarfing of other plant species;

(F) Delay of senescence, especially in flowering plants;

(G) Enhanced viability or improved germination of seed grown on plants treated with the compounds of the present invention.

The advantages obtained with increased internode length are multiple. They include, in addition to a general increase in the total size and weight of the plant, opening or spreading of plant leaves which generally makes the plant less vulnerable to disease through better ventilation. Moreover, increased internode length has particular advantage for crops such as tobacco, sugar cane, timber and seed corn. Elongation of tobacco internodes elevates the lower tobacco leaves from the ground surface sufficiently to prevent their normal destruction or damage by the elements (i.e. abrasion, disease, etc.).

With sugar cane and timber, longer internodes produce larger cane and trees, resulting in greater yields of sugar and lumber; whereas, longer internodes in seed corn raise the corn tassel, i.e. the male organ of the plant, high enough that it can be removed from all plants in a field with a single cutting before pollination occurs. Controlled pollination, to provide a desired hybrid corn, can then be effected at will.

The advantage of increasing the leaf size of plants is obvious and of particular importance for those plants wherein the leaves constitute the marketable crop. Tobacco, forage crops and leafly vegetables such as spinach, swiss chard, lettuce and cabbage exemplify such crops.

Accelerated flowering and bolting is important for crops which are grown for seed including crops such as lettuce, radish, sugar beets, red beets, brussel sprouts, broccoli and carrots. Accelerated flowering effect shows also reduced time to harvest, thus enhancing the possibility of multiple cropping versus single cropping.

Increased set in tuberous plants such as potatoes is another important advantage of this invention, since the treated plants may develop two to three times as many potatoes as the untreated plants. Moreover, the potatoes on treated plants are vastly more uniform than those on untreated plants, although they are only average in size. This, however, is an advantage where the potatoes are to be used for canning. Increased size in certain root crops such as sugar beets may also be obtained with use of the compounds of this invention.

Dwarfing of plants is yet another advantage of the present invention and is of particular importance for treatment of ornamental plants and shrubs.

Another advantage is the finding that seeds obtained from plants treated with the compounds of the present invention are more viable and germinate better than seeds from untreated plants.

A still further advantage obtained with the compounds of the present invention is the delay of senescence in plants. This effect is especially important to nursery men and florists who desire to extend the life of the blooms in flowering plants.

Several of the above plant regulating effects have been noted to increase yields. Yield increases are also obtained in other crops; for example, soybeans, sugar beets, or the like, either as a result of one or more of the above-enumerated growth regulating effects or, perhaps, as a result of a more direct influence on yield.

Surprisingly, we have discovered that the dicarboximido compounds described above provide these advantages.

We have also found that the effectiveness of the compounds of the invention as plant growth regulating agents is not limited by formulation or method of application. The active compounds may be formulated as dusts, dust concentrates, wettable powders, about 80% by weight of a solid carrier such as kaolin. Suitable equipment for such preparations are ribbon-type blenders and double-cone blenders. It is also obvious that the concentration of active ingredient in dust formulations can be readily varied by adjusting the amount of wettable powder and carrier used. Typical dusts will generally vary between about 1% to 15% by weight of active ingredient, although higher concentrations may also be prepared.

An alternative process for preparation of dusts, also dust concentrates, involves blending the active dicarboximide derivative with the solid carrier and passing the uniform blend through an attrition mill to obtain the desired particle size.

A typical granular formulation can be prepared by blending a small amount, i.e. about 0.3% by weight, of a fumed colloidal silica with about 5.6% by weight of the above-said dithiin derivative and air-milling the mixture to a uniform blend. Silica sand, about 85.7% by weight, is then placed in a blender along with about 0.7% by weight of calcium-sodium lignin suflonate powder and 4.2% of a 1% aqueous solution of calcium-sodium lignin sulfonate. The mixture is blended and then 3.5% by weight of synthetic calcium silicate is added. The mixture is permitted to continue blending for several minutes until the finished product is uniformly coated and free flowing. It is, of course, obvious that the amount of active ingredient in the formulated granular product can be widely varied, preferably between about 1% to 15% by weight. This simply requires appropriate adjustment of the amount of granular carrier used and/or adjuvants added. It is likewise obvious that sorptive granular carriers, as well as non-sorptive carriers, can be employed in the preparation of the granular formulations.

Other formulations, methods, products and advantages of the present invention may become apparent from the examples set forth below. These examples are provided simply as an illustration of the invention and are not intended to be limiting thereon.

EXAMPLE 1

Preparation of 5,6-Dihydro-5-phenyl-p-dithiin-2,3-dicarboxylic anhydride.

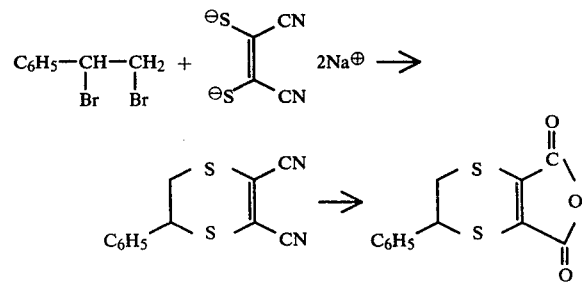

To a stirred suspension of 18.6 g of the disodium salt of 1,2-dicyano-1,2-dimercaptoethylene under nitrogen is added 26.4 g of 1,2-dibromo-1-phenylethane. After stirring at 40° C. for one-half hour, the mixture is heated under reflux for 1.5 hours, cooled, filtered, and the solvent removed under reduced pressure. The residue is crystallized by filtration with carbon tetrachloride to give the product, 2,3-dicyano-5,6-dihydro-5-phenyl-p-dithiin, as golden brown crystals, melting point 121.5° C. to 124° C. A purified sample had melting point 125° C. to 126.5° C.

Hydrolysis of the dinitrile is accomplished by stirring 16.0 g dinitrile in 71 ml concentrated sulfuric acid and adding slowly 66 ml water so that the temperature of the mixture reaches approximately 120° C. The mixture is held at this temperature for 5 hours after which it is poured on ice, the resulting precipitate filtered, washed with water and air-dried. This solid is recrystallized from chloroform to give the desired product, melting point 131° C. to 133° C. The analytical sample is obtained from methylcyclohexane and has melting point 139° C. to 139.5° C.

EXAMPLE 2

Preparation of 5-Substituted-5,6-dihydro-p-dithiin-2,3-dicarboxylic anhydrides

Utilizing the procedure set forth in Example 1, but substituting the appropriate substituted-1-phenyl-1,2-dibromoethane or 1,2-dibromopropane for 1,2-dibromo-1-phenylethane, the following 5,6-dihydro-p-dithiin-2,3-dicarboxylic anhydrides are prepared.

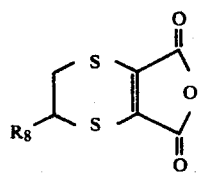

$R_8 = CH_3-$ (melting point 173° C. to 174° C.),

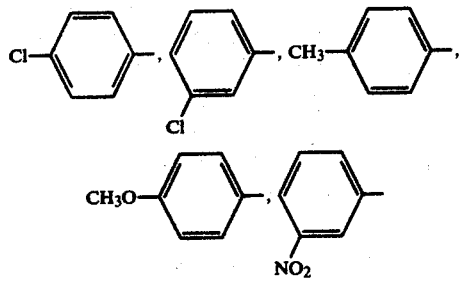

EXAMPLE 3

Preparation of 1-(5,6-Dihydro-p-dithiin-2,3-dicarboximido)cyclohexanecarboxylic acid

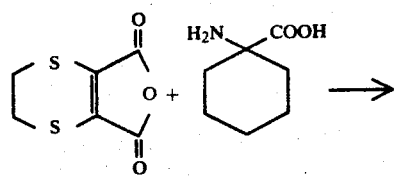

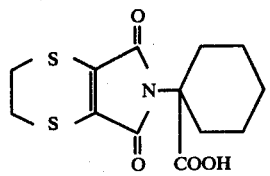

A stirred mixture containing 7.3 g of 1-aminocyclohexanecarboxylic acid, 9.4 g of 5,6-dihydro-p-dithiin-2,3-dicarboxylic anhydride and 1 ml of triethylamine in 150 ml xylene is heated under reflux under a Dean-Stark water separator for 16 hours. The hot solution is filtered, and the filtrate reduced in volume to 50 ml. The mixture is cooled, and the product, 1-(5,6-dihydro-p-dithiin-2,3-dicarboximido)cyclohexanecarboxylic acid, melting point 187° C. to 188.5° C., removed by filtration and air-dried. The crude product is recrystallized from xylene to give an analytically pure sample, melting point 189° C. to 190° C.

Analysis. Calculated for $C_{13}H_{15}NO_4S_2$: C, 49.82; H, 4.82; N, 4.47. Found: C, 50.19; H, 4.59; N, 4.28.

EXAMPLE 4

Preparation of 1-(5,6-Dihydro-p-dithiin-2,3-dicarboximido)cyclopentanecarboxylic acid

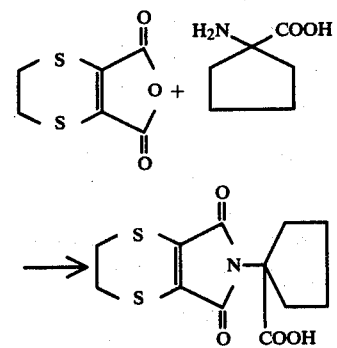

Following the procedure described in Example 3, but substituting 1-aminocyclopentanecarboxylic acid for 1-aminocyclohexanecarboxylic acid, the product, 1-(5,6-dihydro-p-dithiin-2,3-dicarboximido)cyclopentanecarboxylic acid, is obtained, which can be recrystallized from toluene, melting point 169° C. to 170° C.

Analysis. Calculated for $C_{12}H_{13}NO_4S_2$: C, 48.15; H, 4.38; N, 4.68. Found: C, 48.52; H, 4.25; N, 4.64.

Other 5,6-dihydro-p-dithiin-2,3-dicarboximidocarboxylic acids which can be prepared by the above procedure, but substituting the appropriate α-aminocarboxylic acid for 1-aminocyclopentanecarboxylic acid, are reported in Table I below.

TABLE I $$\underset{R_8}{\overset{S}{\underset{S}{\bigg\langle}}}\hspace{-2pt}\underset{O}{\overset{O}{=}}\hspace{-2pt}N-\underset{R_2}{\overset{R_1}{C}}-COOH$$

| $R_8$ | $R_1$ | $R_2$ | Solvent | Melting Point °C. |
|---|---|---|---|---|
| H | $CH_3$ | $-CH_2CH(CH_3)_2$ | Xylene | |
| H | $CH_3$ | $-CH_2CH_2CH_3$ | Xylene | |
| H | $-(CH_2)_7-$ | | Xylene | |
| H | $-(CH_2)_6-$ | | Toluene | |
| H | $CH_3$ | $-CH(CH_3)_2$ | Toluene | 188.5–189.5 |
| H | $C_2H_5$ | $-C_2H_5$ | Xylene | |
| H | $C_2H_5$ | $-CH(CH_3)_2$ | Xylene | |
| H | $C_2H_5$ | $-CH_2CH(CH_3)_2$ | Toluene | |
| H | $C_3H_7$ | $-C_3H_7$ | Toluene | |
| H | $-(CH_2)_3-$ | | Xylene | |
| H | $\underset{-CH_2-CH-CH_2-CH_2-CH_2-}{CH_3}$ | | Xylene | 222–223 |
| $CH_3$ | $-(CH_2)_5-$ | | Xylene | |
| $C_6H_5$ | $-(CH_2)_5-$ | | Acetic Acid | |
| $Cl-\!\!\bigcirc\!\!-$ | $-(CH_2)_5-$ | | Acetic Acid | |
| $CH_3-\!\!\bigcirc\!\!-$ | $-(CH_2)_5-$ | | Acetic Acid | |
| $CH_3O-\!\!\bigcirc\!\!-$ | $-(CH_2)_5-$ | | Acetic Acid | |
| $\underset{NO_2}{\bigcirc}-$ | $-(CH_2)_5-$ | | Acetic Acid | |

EXAMPLE 5

Preparation of 1-(5,6-Dihydro-p-dithiin-2,3-dicarboximido)cyclohexanecarbonyl chloride

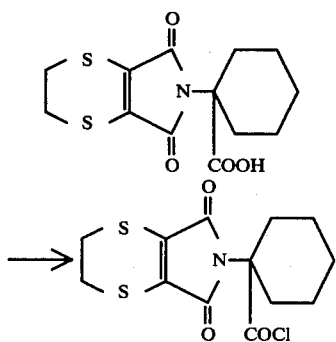

A stirred mixture containing 6.0 g of 1-(5,6-dihydro-p-dithiin-2,3-dicarboximido)cyclohexanecarboxylic acid and 1.8 ml thionyl chloride in 50 ml benzene is heated under reflux for 3.5 hours. The solvent and excess thionyl chloride are removed under reduced pressure, and the residual oil, characterized only by its infrared spectrum, is essentially pure 1-(5,6-dihydro-p-dithiin-2,3-dicarboximido)cyclohexanecarbonyl chloride.

EXAMPLE 6

Preparation of 1-(5,6-Dihydro-p-dithiin-2,3-dicarboximido)cyclopentanecarbonyl chloride

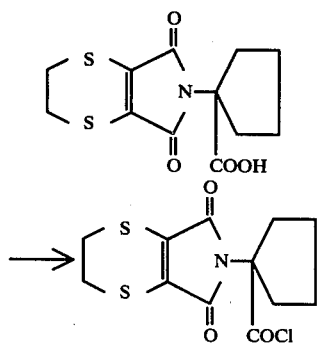

Using the procedure set forth in Example 5, but substituting 1-(5,6-dihydro-p-dithiin-2,3-dicarboximido)cyclopentanecarboxylic acid for 1-(5,6-dihydro-p-dithiin-2,3-dicarboximido)cyclohexanecarboxylic acid, the product, 1-(5,6-dihydro-p-dithiin-2,3-dicarboximido)cyclopentanecarbonyl chloride is obtained, characterized only by its infrared spectrum.

This procedure is repeated, but substituting the appropriate acid for 1-(5,6-dihydro-p-dithiin-2,3-dicarboximido)cyclopentanecarboxylic acid to yield the compounds given in Table II below.

TABLE II

| $R_8$ | $R_1$ | $R_2$ |
|---|---|---|
| H | | $-(CH_2)_7-$ |
| H | | $-(CH_2)_6-$ |
| H | | $-(CH_2)_3-$ |
| H | $CH_3$ | $-CH(CH_3)_2$ |
| H | $CH_3$ | $-CH_2CH(CH_3)_2$ |
| H | $CH_3$ | $-CH_2CH_2CH_3$ |
| H | $C_2H_5$ | $-C_2H_5$ |
| H | $C_2H_5$ | $-CH(CH_3)_2$ |
| H | $C_3H_7$ | $-C_3H_7$ |
| H | | $-CH_2-\overset{CH_3}{\underset{|}{CH}}-CH_2-CH_2-CH_2-$ |
| $CH_3$ | | $-(CH_2)_5-$ |
| $C_6H_5$ | | $-(CH_2)_5-$ |
| Cl-C6H4- | | $-(CH_2)_5-$ |
| CH3-C6H4- | | $-(CH_2)_5-$ |
| CH3O-C6H4- | | $-(CH_2)_5-$ |
| NO2-C6H4- | | $-(CH_2)_5-$ |

EXAMPLE 7

Preparation of
1-(5,6-Dihydro-p-dithiin-2,3-dicarboximido)cyclohexanecarboxamide

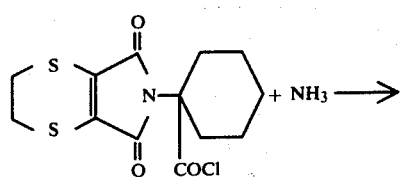 + NH₃ →

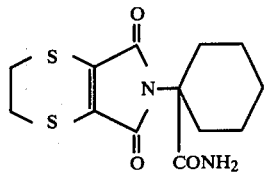

The 1-(5,6-dihydro-p-dithiin-2,3-dicarboximido)cyclohexanecarbonyl chloride prepared in Example 5 is dissolved in 100 ml tetrahydrofuran and cooled to 5° C. Ammonia gas is bubbled through the stirred solution until a slight excess is added. The mixture is filtered to remove inorganic salts, the filtrate concentrated at reduced pressure and the residue crystallized from methanol to give 1-(5,6-dihydro-p-dithiin-2,3-dicarboximido)cyclohexanecarboxamide, melting point 188° C. to 189.5° C.

Analysis. Calculated for $C_{13}H_{16}N_2O_3S_2$: C, 49.98; H, 5.16; N, 8.97. Found: C, 50.02; H, 5.08; N, 8.75.

EXAMPLE 8

Preparation of
1-(5,6-Dihydro-p-dithiin-2,3-dicarboximido)cyclopentanecarboxamide

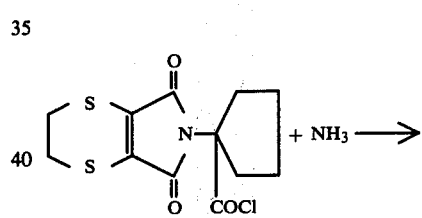 + NH₃ →

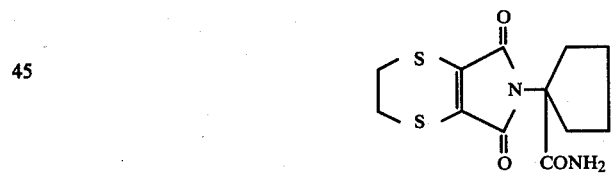

Using the procedure set forth in Example 7, but substituting 1-(5,6-dihydro-p-dithiin-2,3-dicarboximido)cyclopentanecarbonyl chloride for 1-(5,6-dihydro-p-dithiin-2,3-dicarboximido)cyclohexanecarbonyl chloride, the product, 1-(5,6-dihydro-p-dithiin-2,3-dicarboximido)cyclopentanecarboxamide, is obtained, melting point 195° C. to 196° C.

Analysis. Calculated for $C_{12}H_{14}N_2O_3S_2$: C, 48.30; H, 4.73; N, 9.39. Found: C, 48.44; H, 4.72; N, 9.46.

The carboxamides of Table III, below, are prepared by the above procedure, but substituting the appropriate acid chloride for 1-(5,6-dihydro-p-dithiin-2,3-dicarboximido)cyclopentanecarbonyl chloride.

TABLE III

[Structure: dithiin-dicarboximide with R8 substituent, N-C(R1)(R2)-CONH2]

| R₁ | R₂ | R₈ | Melting Point °C. |
|---|---|---|---|
| —(CH₂)₃— | | H | |
| —(CH₂)₇— | | H | |
| —(CH₂)₆— | | H | |
| CH₃ | —CH₂CH₂CH₃ | H | |
| C₂H₅ | —C₂H₅ | H | |
| CH₃ | —CH(CH₃)₂ | H | 184–186.5 |
| CH₃ | —CH₂CH(CH₃)₂ | H | 163–164 |
| C₂H₅ | —CH(CH₃)₂ | H | |
| C₃H₇ | —C₃H₇ | H | 238–239 |
| —CH₂—CH(CH₃)—CH₂—CH₂—CH₂— | | H | |
| —(CH₂)₅— | | CH₃ | 129–131 |
| —(CH₂)₅— | | C₆H₅ | 100–112 (decomp.) |
| —(CH₂)₅— | | 4-Cl-C₆H₄— | |
| —(CH₂)₅— | | 4-CH₃-C₆H₄— | |
| —(CH₂)₅— | | 4-CH₃O-C₆H₄— | |
| —(CH₂)₅— | | 3-NO₂-C₆H₄— | |

EXAMPLE 9

Preparation of 1-(5,6-Dihydro-p-dithiin-2,3-dicarboximido)N,N-dimethylcyclohexanecarboxamide

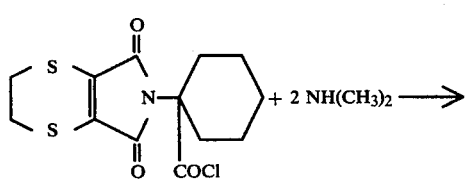

A solution containing 10 g of 1-(5,6-dihydro-p-dithiin-2,3-dicarboximido)cyclohexanecarbonyl chloride in 50 ml tetrahydrofuran is cooled to 10° C. to 15° C., and while stirring, gaseous dimethylamine is bubbled into the solution until saturated. After a further 5 minutes, the mixture is filtered to remove salts and the solvent removed from the filtrate to give the above-named product, melting point 169° C. to 170.5° C.

The N-substituted carboxamides of Table IV, below, are prepared using essentially the same procedure described above.

TABLE IV

[Structure: dithiin-dicarboximide with R8, N-C(R1)(R2)-CONR4R5]

| R₁ | R₂ | R₄ | R₅ | R₈ | Melting Point °C. |
|---|---|---|---|---|---|
| —(CH₂)₄— | | CH₃ | CH₃ | H | — |
| —(CH₂)₆— | | CH₃ | CH₃ | H | — |
| —(CH₂)₅— | | H | 4-CH₃O-C₆H₄— | H | 225–226 |

TABLE IV-continued

| R₁ | R₂ | R₄ | R₅ | R₈ | Melting Point °C. |
|---|---|---|---|---|---|
| —(CH₂)₅— | | H | (2-chlorophenyl) | H | 129–130 |
| —(CH₂)₅— | | H | CH₃ | H | 178–179 |

EXAMPLE 10

Preparation of 1-(5,6-Dihydro-p-dithiin-2,3-dicarboximido)cyclohexanecarboxylic acid, 2,2-Dimethylhydrazide.

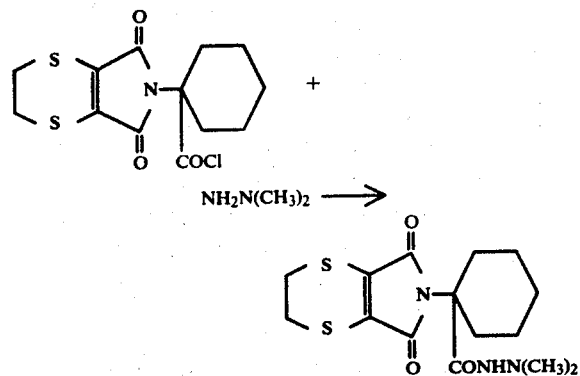

To an ice-cold solution of acid chloride in tetrahydrofuran is added dropwise two equivalents of 1,1-dimethylhydrazine. After stirring a further 0.5 hour, the solids are removed by filtration and the solvent removed in vacuo from the filtrate to give the abovenamed product, melting point 149° C. to 150° C.

EXAMPLE 11

Preparation of 2-[1-(5,6-Dihydro-p-dithiin-2,3-dicarboximido)cyclohexylcarbonyl]-1,1,1-trimethylhydrazinium bromide.

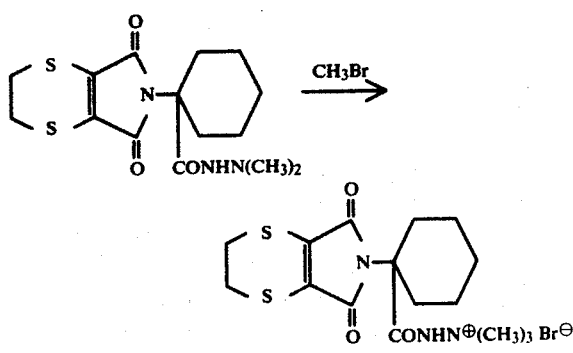

To the dimethylhydrazide prepared, as described in Example 10, is added excess methyl bromide and the mixture stirred in a pressure bottle for two days. Excess methyl bromide was removed by evaporation to leave the quaternary bromide, melting point 176° C. to 177° C. The bromide can be converted to the chloride by passing a 50% aqueous ethanol solution of the salt slowly down a column packed with Amberlyst A21, an organic ion exchange resin, in its chloride form, and evaporating the eluent. The residue is crystallized from ethanol-ether to give the chloride salt.

EXAMPLE 12

Preparation of Ethyl 1-(5,6-dihydro-p-dithiin-2,3-dicarboximido)cyclohexanecarboxylate.

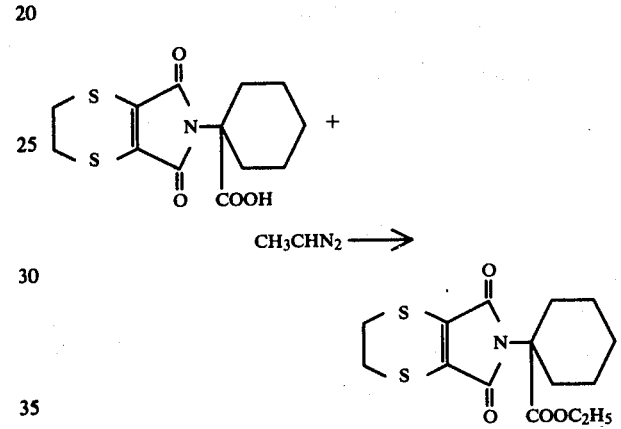

An excess of an ether solution of diazoethane is added to a solution of 1-(5,6-dihydro-p-dithiin-2,3-dicarboximido)cyclohexanecarboxylic acid in ether. After standing for one hour at room temperature, the solution is washed with excess aqueous sodium carbonate solution, followed by two water washes. The organic phase is dried and the solvent evaporated under reduced pressure to give the abovenamed product.

Alternatively, this ester can be prepared by the action of ethanol and pyridine on the acid chloride, described in Example 5.

EXAMPLE 13

Preparation of 3-[N-(1-cyanocyclohexyl)carbamoyl]5,6-dihydro-p-dithiin-2-carboxylic acid.

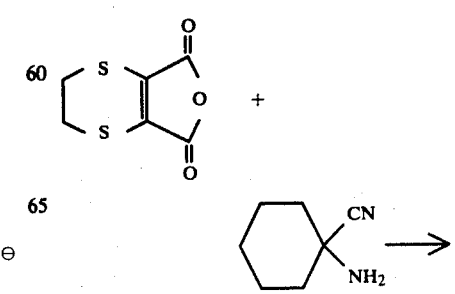

-continued

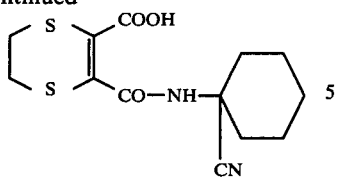

To a stirred suspension of 1.88 g anhydride in 50 ml ether is added 1.24 g of the aminonitrile. The mixture is heated under reflux for 5 hours. The crystalline product is removed by filtration, washed with acetonitrile and dried to give the title compound, melting point 133° C. to 134° C. (decomp.).

EXAMPLE 14

Preparation of 1-(5,6-Dihydro-p-dithiin-2,3-dicarboximido)cyclohexanecarbonitrile.

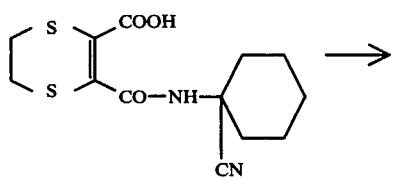

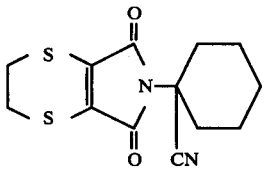

A suspension of the acid in acetonitrile is heated under reflux for 3 hours. The colorless solid dissolves to give a bright yellow solution. The solvent is removed and the residue crystallized from methanol to give the title compound, melting point 123° C. to 124° C.

Analysis Calculated for $C_{13}H_{14}N_2O_2S_2$: C, 53.04; H, 4.79; N, 9.52. Found: C, 53.31; H, 4.94; N, 9.58.

EXAMPLE 15

Preparation of 1-(5,6-Dihydro-p-dithiin-2,3-dicarboximido)cyclohexanecarboxamide.

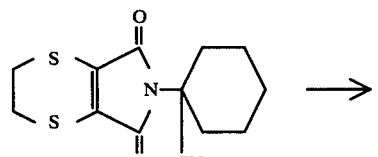

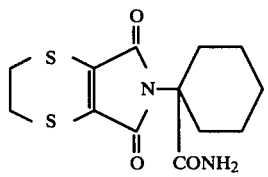

To 300 mg of nitrile in 5 ml methylene chloride is added with vigorous stirring 10 drops concentrated sulfuric acid. After 0.5 hour ice and more methylene chloride is added. The organic phase is separated, washed with water, dried and the solvent evaporated leaving a crystalline residue of the title compound, melting point 187° C. to 189° C.

EXAMPLE 16

Preparation of Methyl 1-(5,6-dihydro-p-dithiin-2,3-dicarboximido)cyclohexanecarboxylate.

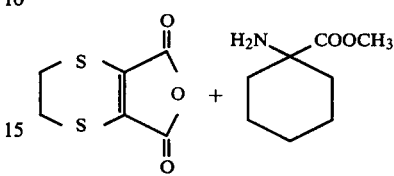

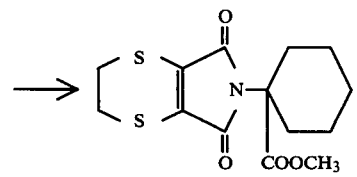

A mixture containing 18.8 g of 5,6-dihydro-p-dithiin-2,3-dicarboxylic anhydride, 15.7 g of the amino ester and 1.3 ml triethylamine in 300 ml xylene is heated with stirring for 6 hours under a Dean-Stark water separator. The solvent is removed, the residue taken up in ether, filtered, and the filtrate washed with sodium bicarbonate solution. The organic phase is separated, dried, and the solvent removed to leave a crystalline residue of the desired product, melting point 96° C. to 99° C.

EXAMPLE 17

Preparation of 1-(5,6-Dihydro-p-dithiin-2,3-dicarboximido)cyclohexanecarboxamide 5-oxide.

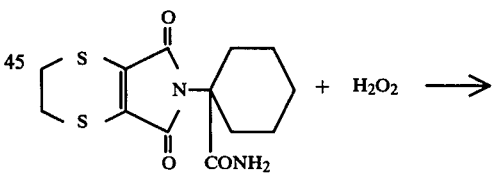

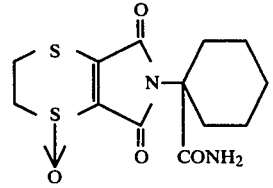

To a stirred suspension of 6.25 g of 1-(5,6-dihydro-p-dithiin-2,3-dicarboximido)cyclohexanecarboxamide in 30 ml acetic acid is added 2.5 g of a 30% aqueous solution of hydrogen peroxide. After 16 hours at 25° C., the solvents are removed in vacuo and the residue taken up in chloroform which is dried and evaporated. The crystalline residue is recrystallized from a 1:1 mixture of chloroform and acetonitrile to give the 5-oxide, melting point 133° C. to 136.5° . (decomp.).

EXAMPLE 18

Preparation of 1-(Tetrahydro-p-dithiin-2,3-dicarboximido)cyclohexanecarboxylic acid.

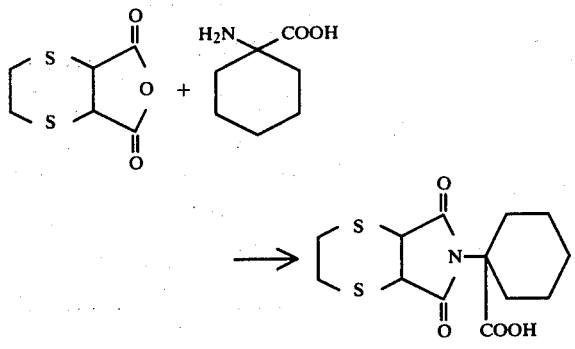

Following the procedure described in Example 3, but substituting tetrahydro-p-dithiin-2,3-carboxylic anhydride for 1-(5,6-dihydro-p-dithiin-2,3-dicarboxylic anhydride and benzene for xylene as the solvent, the product described in the title is prepared, melting point 63° C. (decomp.).

EXAMPLE 19

Preparation of 1-(Tetrahydro-p-dithiin-2,3-dicarboximido)cyclohexanecarbonyl chloide.

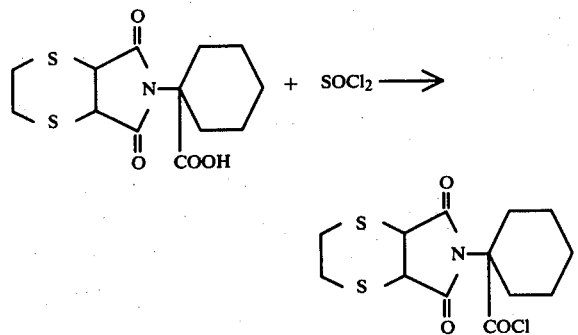

Using the procedure set forth in Example 5, but substituting 1-(tetrahydro-p-dithiin-2,3-dicarboximido)cyclohexanecarboxylic acid for 1-(5,6-dihydro-p-dithiin-2,3-dicarboximido)cyclohexanecarboxylic acid, the product described in the title is obtained, characterized only by its infrared spectrum.

EXAMPLE 20

Preparation of 1-(Tetrahydro-p-dithiin-2,3-dicarboximido)cyclohexanecarboxamide.

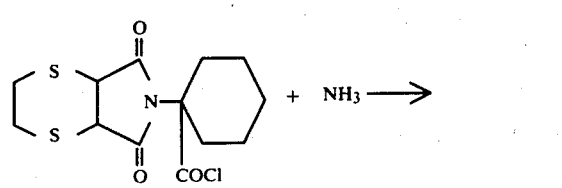

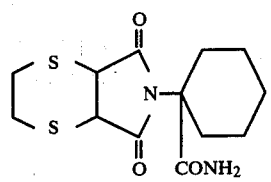

Using the procedure set forth in Example 7, but substituting 1-(tetrahydro-p-dithiin-2,3-dicarboximido)cyclohexanecarbonyl chloride for 1-(5,6-dihydro-p-dithiin-2,3-dicarboximido)cyclohexanecarbonyl chloride, the product described in the title, melting point 188° C. to 189° C. is obtained.

EXAMPLE 21

Preparation of 1-(2,2-Dimethyl-1,3-dithiolane-4,5-dicarboximido)cyclohexanecarboxylic acid.

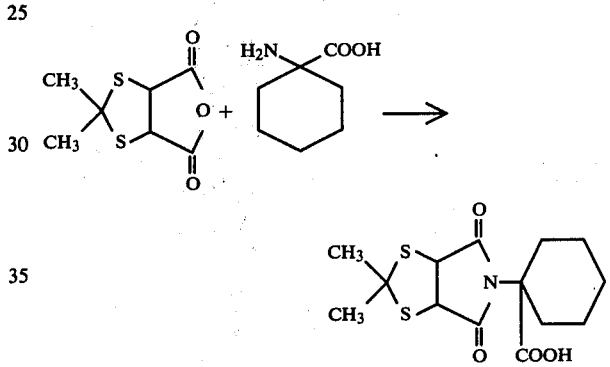

A stirred mixture of 10.2 g of 2,2-dimethyl-1,3-dithiolane-4,5-dicarboxylic anhydride and 7.1 g of amino acid in 170 ml benzene and 0.5 ml triethylamine is heated under reflux under a Dean-Stark water separator for 48 hours. The solvent is removed and the residue crystallized from aqueous methanol to give the title product, melting point 188° C. to 189° C.

Other 1,3-dithiolane-4,5-dicarboximidocarboxylic acids which can be prepared by the above procedure, but substituting the appropriate anhydride for 2,2-dimethyl-1,3-dithiolane-4,5-dicarboxylic anhydride, are reported below.

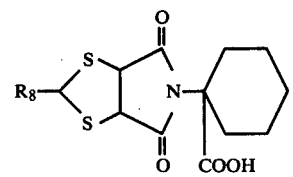

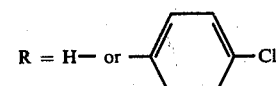

EXAMPLE 22

Preparation of
1-(2,2-Dimethyl-1,3-dithiolane-4,5-dicarboxyimido)cyclohexanecarbonyl chloride.

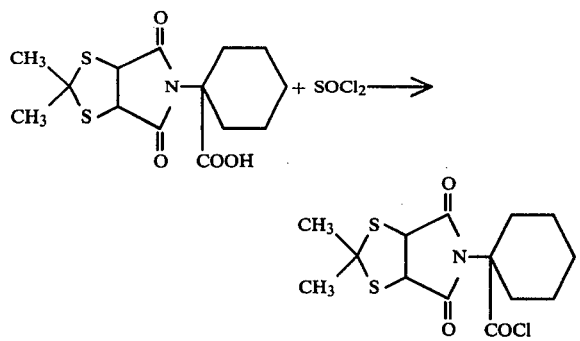

Using the procedure set forth in Example 5, but substituting 1-(2,2-dimethyl-1,3-dithiolane-4,5-dicarboximido)cyclohexanecarboxylic acid for 1-(5,6-dihydro-p-dithiin-2,3-dicarboximido)cyclohexanecarboxylic acid, the product described in the title is obtained, characterized only by its infrared spectrum.

By substituting the appropriate acid described in Example 21, the following carbonyl chlorides are prepared.

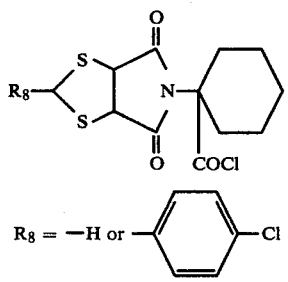

EXAMPLE 23

Preparation of
1-(2,2-Dimethyl-1,3-dithiolane-4,5-dicarboximido)cyclohexanecarboxamide.

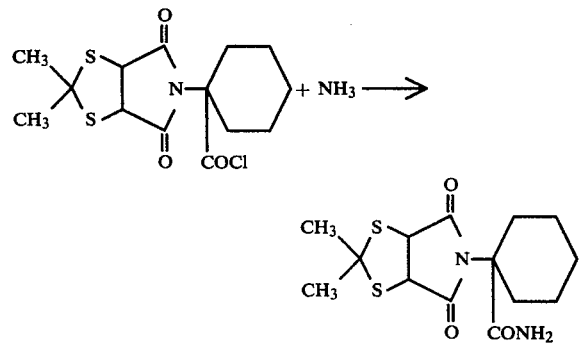

Using the procedure set forth in Example 7, but substituting 1-(2,2-dimethyl-1,3-dithiolane-4,5-dicarboximido)cyclohexanecarbonyl chloride for 1-(5,6-dihydro-p-dithiin-2,3-dicarboximido)cyclohexanecarbonyl chloride, the product described in the title is obtained, melting point 163° C. to 164.5° C.

The carboxamides below are prepared by the above procedure by substituting the appropriate carbonyl chloride of Example 22 for 1-(2,2-dimethyl-1,3-dithiolane-4,5-dicarboximido)cyclohexanecarbonyl chloride.

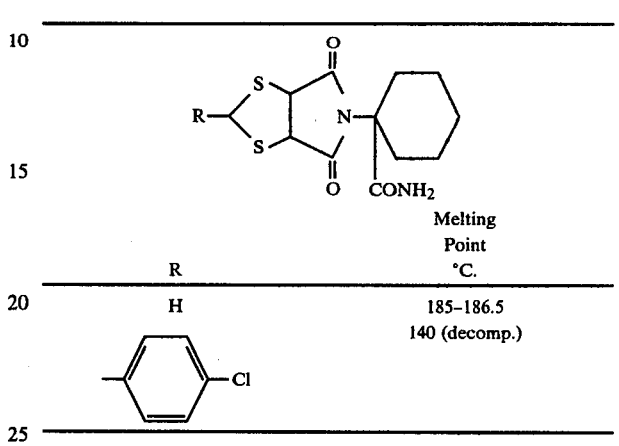

| R | Melting Point °C. |
|---|---|
| H | 185–186.5 |
|  | 140 (decomp.) |
| —⌬—Cl |  |

EXAMPLE 24

Preparation of
1-(5,6-Dihydro-4H-thiapyran-2,3-dicarboximido)cyclohexanecarboxylic acid.

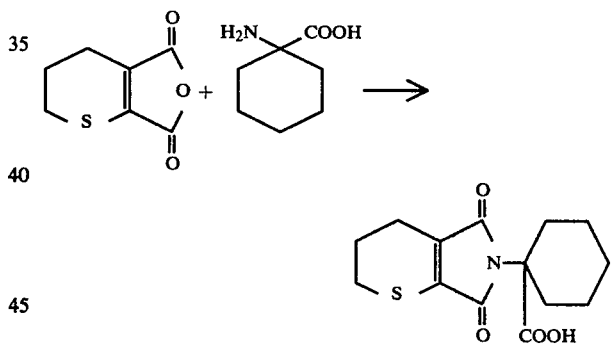

Following the procedure described in Example 3, but substituting 5,6-dihydro-4H-thiapyran-2,3-dicarboxylic anhydride for 5,6-dihydro-p-dithiin-2,3-dicarboxylic anhydride, the product described in the title is obtained as a gum and characterized only by its infrared spectrum.

EXAMPLE 25

Preparation of
1-(5,6-Dihydro-4H-thiapyran-2,3-dicarboximido)cyclohexanecarbonyl chloride.

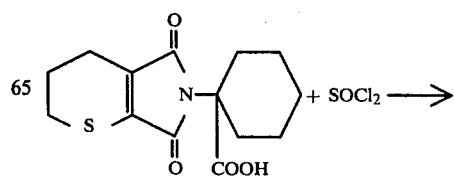

-continued

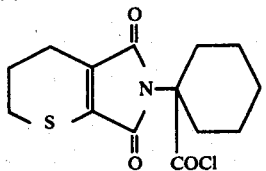

Using the procedure set forth in Exxample 5, but substituting 1-(5,6-dihydro-4H-thiapyran-2,3-dicarboximido)cyclohexanecarboxylic acid for 1-(5,6-dihydro-p-dithiin-2,3-dicarboximido)cyclohexanecarboxylic acid, the product described in the title is obtained, characterized only by its infrared spectrum.

EXAMPLE 26

Preparation of 1-(5,6-Dihydro-4H-thiapyran-2,3-dicarboximido)cyclohexanecarboxamide.

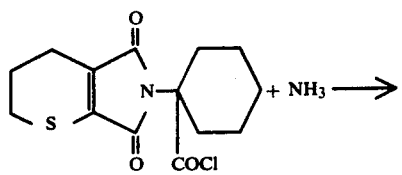

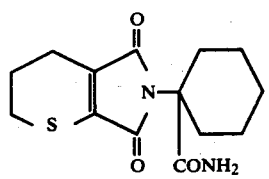

Using the procedure set forth in Example 7, but substituting 1-(5,6-dihydro-4H-thiapyran-2,3-dicarboximido)cyclohexanecarbonyl chloride for 1-(5,6-dihydro-p-dithiin-2,3-dicarboximido)cyclohexanecarbonyl chloride, the product named in the title is obtained as a crystalline solid, melting point 178° C. to 180.5° C.

EXAMPLE 27

Preparation of 1-(6-Methyl-5,6-dihydro-4H-pyran-2,3-dicarboximido)-cyclohexanecarboxylic acid.

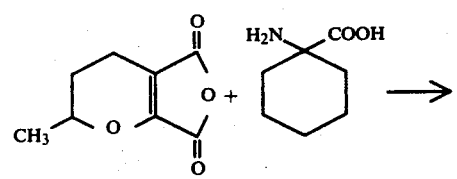

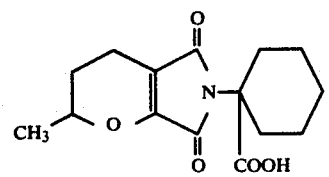

Following the procedure set forth in Example 3, but substituting 6-methyl-5,6-dihydro-4H-pyran-2,3-dicarboxylic anhydride for 5,6-dihydro-p-dithiin-2,3-dicarboximidocarboxylic anhydride, the product described in the title is obtained as a tan solid identified by infrared spectrum.

EXAMPLE 28

Preparation of 1-(6-Methyl-5,6-dihydro-4H-pyran-2,3-dicarboximido)-cyclohexanecarbonyl chloride.

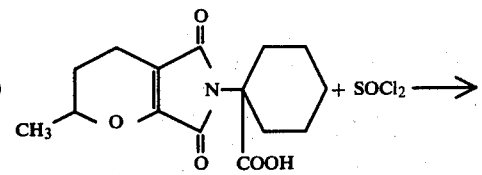

Following the procedure set forth in Example 5, but substituting 1-(6-methyl-5,6-dihydro-4H-pyran-2,3-dicarboximido)cyclohexanecarboxylic acid for 1-(5,6-dihydro-p-dithiin-2,3-dicarboximido)cyclohexanecarboxylic acid, the product described in the title is obtained and characterized only by its infrared spectrum.

EXAMPLE 29

Preparation of 1-(6-Methyl-5,6-dihydro-4H-pyran-2,3-dicarboximido)-cyclohexanecarboxamide.

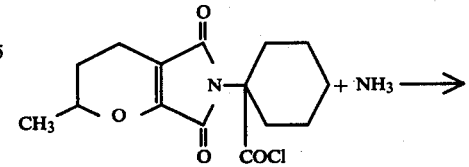

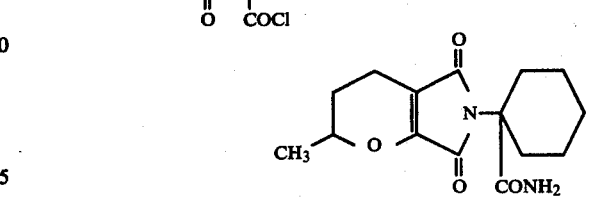

Using the procedure set forth in Example 7, but substituting 1-(6-methyl-5,6-dihydro-4H-pyran-2,3-dicarboximido)cyclohexanecarbonyl chloride for 1-(5,6-dihydro-p-dithiin-2,3-dicarboximido)cyclohexanecarbonyl chloride, the product described in the title was obtained as a crystalline solid, melting point 185.5° C. to 189° C.

EXAMPLE 30

Plant Growth Regulant Evaluation of Biologically Active Compounds.

Test solutions are prepared by dissolving the test compound in a 50/50 acetone/water mixture and adding thereto 0.4% Tween-20 surfactant. A sufficient amount of this solution is then applied to seeded pots or to the foliage of test plants to provide from about ⅛ lb/acre to 8.0 lb/acre of test compound.

Containers used for preemergence treatments are prepared the day before application of the test compounds. Appropriate amounts of soil are placed in the containers to bring the soil level to within ¾ inch of the tops of the containers. Seeds of the plant species are placed on the soil surface after which the seeds are covered with ½ inch of soil. A tamper is used to level the soil surface and to firm the soil.

Plant species used for postemergence testing are planted about 17 days before treatment in appropriate containers, as described for preemergence plantings.

Treatments

Each compound is applied preemergence and postemergence to a variety of plant species. Containers containing the eight plant species are assembled in a galvanized metal flat (14"×22"), one flat for each rate of each compound. Treatment consists of spraying the test solutions at a rate of 86 gallons per acre (gpa) with a nozzle moving over the metal flat at a constant speed.

Untreated plants of each species serve as controls in each test. Plant species employed in preemergence evaluations are corn (Dekalb), lima bean (Henderson bush) and soybean (Amsoy). Plant species used in postemergence evaluations are radish (Cherry Belle), cucumber (Marketer), fescue (Ky. 31) and rice (Nato).

All plant species are observed daily after treatment for changes in physiology and morphology as compared to control plants. Growth changes of interest included are:

(1) Delay or acceleration of leaf or flower senscence,
(2) Change in sex of cucumber flowers,
(3) Advances in flowering of dicot species,
(4) Increased or decreased axillary bud or tiller growth,
(5) Dwarfing or growth stimulation of stems and leaves,
(6) Advances in emergence of species treated with preemergence applications,
(7) Toxic effects on all species.

Such effects were recorded when they occur.

Final data or visual observations are made at 14 days after treatment for radish and fescue and at 25 days after treatment for cucumber, lima beans, soybeans, barley and corn. Table V presents quantitative data and ratings of observable growth effects obtained.

TABLE V

| Structure | Postemergence Evaluation | | |
|---|---|---|---|
| | Rate lb/acre | Plant Species | Observations |
| 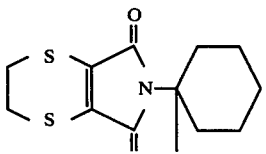 | 0.125 0.5 2.0 8.0 | Radish | Leaves much larger than untreated controls at all rates of application. 20% Total plant weight increase over untreated controls at 0.5 lb/acre rate, 25% plant weight increase at 2 lb/acre rate and 37% plant weight increase at 8 lb/acre rate. |
| 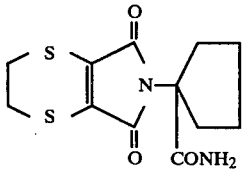 | 0.125 0.5 2.0 | Radish | 40% Increase in total plant weight over untreated controls at 0.125 lb/acre rate, 35% increase in plant weight over untreated controls at 0.5 lb/acre rate and 45% increase in plant weight over untreated controls at 2 lb/acre rate. 50% Root weight increase at 0.125 lb/acre, 45% root weight increase at 0.5 lb/acre and 57% root weight increase at 2 lb/acre. |
| 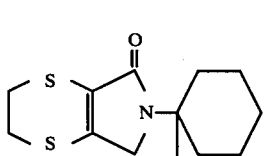 | 0.5 2.0 | Cucumber | Sex expression, 1 female flower produced at 0.5 lb/acre rate and 2 female flowers produced at 2 lb/acre rate. Untreated controls did not flower. |

TABLE VI

| Structure | Preemergence Evaluation | | |
|---|---|---|---|
| | Rate lb/acre | Plant Species | Observations |
| 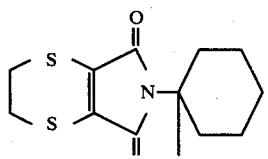 | 2.0 8.0 | Lima bean | 20% Reduction in plant size observed at 2 lb/acre rate and 75% reduction in plant size observed at 8 lb/acre rate. |

TABLE VI-continued

| | Preemergence Evaluation | | |
|---|---|---|---|
| Structure | Rate lb/acre | Plant Species | Observations |
| 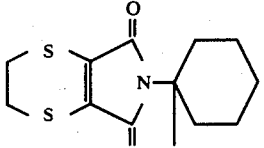 | 8.0 | Soybean | 30% Reduction in plant size observed at 8 lb/acre rate. |

EXAMPLE 31

Increased Internode Growth and Fresh Weight of Corn Plants.

In these tests, corn seeds are placed in rows in a soil surface in flats. A spray, 50/50 acetone/water, containing the test compound is applied over the seed and soil surface in sufficient amount to provide 1, 2, 4 or 8 pounds per acre of test compound. The seed is covered with about ½ inch of untreated soil and then watered. The flats are placed on greenhouse benches and cared for in accordance with greenhouse practices. Three weeks after treatment, the flats are examined and the height and fresh weight of the corn plants cut at the soil line is determined. Data obtained are reported in Table VII below.

plants were drooped. It was further found that all treated plants were caused to bolt. This phenomenon is important and unexpected since sugar beets normally require two years to bolt and seed. This occurrence is especially significant to the farmer who grows sugar beets for seed yield.

EXAMPLE 33

Evaluation of Test Compounds for Plant Growth Enhancement

In these tests, containers are filled to within ½ inch of the top with greenhouse potting soil and tamped. The pot is then filled to the top with soil in which Kentucky 31 Fescue seeds have been mixed in an amount sufficient to provide each pot with approximately 625 Fescue seeds.

TABLE VII

Plant Growth Regulating Effects of Test Compounds

| | | Corn | | | |
|---|---|---|---|---|---|
| Structure | Rate lb/acre | Avg. Height (cm) | % Height Increase | Avg. Weight (gram) | % Weight Increase |
| Acetone/Water Control | — | Replicates { 61 / 57 | — / — | 110 / 101 | — / — |
| 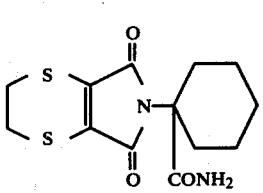 | 1 | 68 | 15 | 147.5 | 39.8 |
| | 2 | 67 | 13 | 139 | 31.7 |
| | 4 | 66 | 11.8 | 142 | 34.6 |
| | 8 | 70 | 18.6 | 141.5 | 34.1 |
| 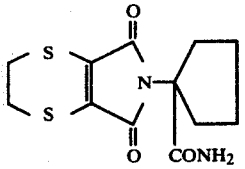 | 1 | 70 | 18.6 | 140 | 32.7 |
| | 2 | 60 | 1 | 114.5 | 8.5 |
| | 4 | 60 | 1 | 131 | 24.1 |
| | 8 | 68 | 15 | 127.5 | 20.8 |

EXAMPLE 32

Enhanced Bolting and Improved Attitude of Leaves on Sugar Beet Plants.

Following the procedure of Example 31, but substituting sugar beet seeds for corn seeds, it was observed that sugar beet plants emerged in a manner similar to untreated plants. However, the plants treated with 1-(5,6-dihydro-p-dithiin-2,3-dicarboximido)cyclohexanecarboxamide and 1-(5,6-dihydro-p-dithiin-2,3-dicarboximido)cyclopentanecarboxamide, at the 1, 2, 4 and 8 pound per acre rate, all grew faster than the untreated controls. It was also observed that the attitude of the leaves of treated plants was more upright and better positioned to intercept light energy for manufacturing food during photosynthesis. The leaves of untreated To prepare the test compounds, 20 mg of the compound is placed into a two-ounce, wide-mouth glass bottle and dissolved or dispersed in a 50/50 acetone/water mixture sufficient to prepare a 1,000 ppm solution or suspension.

An addition of 5 ml of the 1,000 ppm solution in each cup is equivalent to 10 lb/acre.

Just prior to the application of the compounds, the test pots are lightly watered to prevent formation of air pockets and channeling routes during application which would prevent even distribution of the test compound in the soil. Application is accomplished by dispensing 5 ml of solution or suspension evenly over the surface of the soil with a pipettor. Three replications are used for each compound.

Each test includes 5 ml of 1:1 acetone:water controls, 5 ml water controls as a standard for comparison of activity from test to test. The treated plants are benched in the greenhouse and normal watering practices are followed. Minimum day and night temperatures of 65° F. are maintained during cooler portions of the year. Normal daily temperature fluctuations occur during the summer season. Data obtained are reported below.

DATA RECORDING

Initial observations are made at three to five days after treatment for early germination of both test species. Physiological or morphological changes from the norm are noted during the test period. Final observations are made at two to three weeks after treatment (dependent on time of year). At this time, measurements of the height of plants are made.

TABLE VIII

Effect of Test Compounds on Height of Fescue

| Compound | Rate lb/Acre | Height of Fescue (cm) |
|---|---|---|
| Water | — | 16 |
| 1-(5,6-dihydro-p-dithiin-2,3-dicarboximido)cyclohexanecarboxamide | 10 | 27 |
| 1-(5,6-dihydro-p-dithiin-2,3-dicarboximido)cyclopentanecarboxamide | 10 | 19 |
| 1-(5,6-dihydro-5-methyl-p-dithiin-2,3-dicarboximido)cyclohexanecarboxamide | 10 | 25 |

EXAMPLE 34

Evaluation of Test Compounds for Increasing the Internode Length and/or the Height of Plants The growth-enhancing activity of the compounds of this invention is exemplified by the following tests in which the seeds of a variety of monocotyledonous and dicotyledonous plants are separately mixed with potting soil and a ½ inch layer of this seed-soil mix is placed on top of approximately 1½ inches of potting soil in separate 2½"×2½" plastic pots. After planting, the cups are sprayed with an aqueous-acetone solution containing test compound in sufficient quantity to provide the equivalent of 10 pounds per acre of test compound per cup. The treated cups are then placed on greenhouse benches, watered and cared for in accordance with greenhouse procedures. Three or four weeks after treatment, the tests are terminated and each cup is examined and rated. The results are set forth below.

Plant Species Used in These Evaluations

| Common Name | Abbreviation | Scientific name |
|---|---|---|
| Nutsedge | NS | *Cyperus rotundus* |
| Lambsquarters | LA | *Chenopodium album* |
| Wild Mustard | MU | *Brassica kaber* |
| Pigweed | PI | *Amaranthus retroflexus* |
| Ragweed | RW | *Ambrosia artemisiifolia* |
| Morningglory | MG | *Ipomoea purpurea* |
| Barnyardgrass | BA | *Echinochloa crusgalli* |
| Crabgrass | CR | *Digitaria sanguinalis* |
| Green Foxtail | FO | *Seteria viridis* |
| Wild Oats | WO | *Avena fatua* |
| Tomato | TO | *Lycopersicon esculentum* |

-continued

Plant Species Used in These Evaluations

| Common Name | Abbreviation | Scientific name |
|---|---|---|
| Velvetleaf | VL | *Abutilon theophrasti* |

Test Results

| Compound | Plant Species Elongated | Approximate Increase in Height |
|---|---|---|
| 1-(5,6-Dihydro-p-dithiin-2,3-dicarboximido)cyclohexane-carboxamide | NS | 2X |
|  | BA | 2X |
|  | CR | 2X |
|  | TO | 2X |
|  | VL | 2X |
| 2,3,5,7-Tetrahydro-α-isobutyl-α-methyl-5,7-dioxo-6H-p-dithiino-[2,3-c]pyrrole-6-acetamide | NS | 2X |
|  | MG | 2X |
| 1-(5,6-Dihydro-5-methyl-p-dithiin-2,3-dicarboximido)cyclohexane-carboxamide | NS | 3-4X |
|  | LA | 3-4X |
|  | BA | 3-4X |
|  | CR | 3-4X |
|  | FO | 3-4X |
|  | TO | 3-4X |
|  | VL | 3-4X |
| 1-(6-Methyl-5,6-dihydro-4H-pyran-2,3-dicarboximido)cyclohexane-carboxamide | NS | 2X |
|  | BA | 2X |
|  | WO | 2X |
| 1-(3,4-Dihydro-2H-thiopyran-5,6-dicarboximido)cyclohexane-carboxamide | NS | 3-4X |
|  | LA | 3-4X |
|  | MG | 3-4X |
|  | BA | 3-4X |
|  | CR | 3-4X |
|  | FO | 3-4X |
|  | WO | 3-4X |
|  | TO | 3-4X |
|  | VL | 3-4X |

We claim:
1. A compound of the formula:

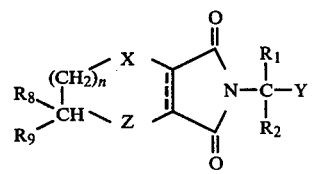

wherein
X is $CH_2$ or S;
Z is S, O, or SO, provided that when Z is O, X cannot be S;
Y is —$COOR_3$, —$CONR_4R_5$, —CONHOH, —$CONHNR_6R_7$, —$CONHN^{\oplus}R_6R_7R_7 \bullet halide^{\ominus}$, CN or —$COR_{10}$;
n is 0 or 1; $R_1$ and $R_2$ each represent alkyl $C_1-C_4$, or when taken together with the carbon to which they are attached form cycloalkyl $C_4-C_8$ or methyl-substituted cycloalkyl $C_4-C_9$;
$R_3$ is hydrogen or alkyl $C_1-C_4$;
$R_4$ and $R_5$ each represent hydrogen, alkyl $C_1-C_4$, phenyl, monohalophenyl, monoalkyl($C_1-C_4$)phenyl, or monoalkoxy($C_1-C_4$)phenyl;
$R_6$ and $R_7$ are alkyl $C_1-C_2$;
$R_8$ is mononitrophenyl hydrogen, alkyl $C_1-C_4$, phenyl, monohalophenyl, monoalkyl($C_1-C_4$)phenyl, monoalkoxy($C_1-C_4$)phenyl or trifluoromethylphenyl;

$R_9$ is hydrogen or alkyl $C_1$-$C_4$;

$R_{10}$ is halogen, and ⎓ represents a single or double bond.

2. A compound according to claim 1 of the formula:

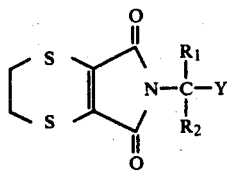

wherein

Y is —$COOR_3$, —$CONR_4R_5$, —$CONHNR_6R_7$, —$CONHN^{\oplus}R_6R_7R_7 \cdot halide^{\ominus}$, CN or —$COR_8$;

$R_1$ and $R_2$ each represent alkyl $C_1$-$C_4$ or when taken together with the carbon to which they are attached form cycloalkyl $C_4$-$C_8$;

$R_3$, $R_4$ and $R_5$ each represent hydrogen or alkyl $C_1$-$C_4$;

$R_6$ and $R_7$ are alkyl $C_1$-$C_2$, either the same or different;

and $R_8$ is halogen.

3. A compound according to claim 1, wherein X and Z are each sulfur, and Y, n, $R_1$, $R_2$, $R_8$ and $R_9$ are as defined in said claim 1.

4. A compound according to claim 1, wherein X is $CH_2$; Z is oxygen, and n, $R_1$, $R_2$, $R_8$ and $R_9$ are as defined in said claim 1.

5. A compound according to claim 1, wherein X is $CH_2$; Z is sulfur, and n, Y, $R_1$, $R_2$, $R_8$ and $R_9$ are as defined in said claim 1.

6. A compound according to claim 1, wherein X is S; Z is SO; and n, Y, $R_1$, $R_2$, $R_8$ and $R_9$ are as defined in said claim 1.

7. A compound according to claim 3, wherein ⎓ is a double bond.

8. A compound according to claim 3, wherein ⎓ is a single bond.

9. A compound according to claim 7, wherein Y is —$CONR_4R_5$.

10. A compound according to claim 7, wherein Y is —$COOR_3$.

11. A compound according to claim 7, wherein Y is —$CONHNR_6R_7$.

12. A compound according to claim 7, wherein Y is —$CONHN^{\oplus}R_6R_7R_7 \cdot halide^{\ominus}$.

13. A compound according to claim 7, wherein Y is —$COR_{10}$.

14. A compound according to claim 9, 1-(5,6-dihydro-p-dithiin-2,3-dicarboximido)cyclohexanecarboxamide.

15. A compound according to claim 9, 1-(5,6-dihydro-p-dithiin-2,3-dicarboximido)cyclopentanecarboxamide.

16. A compound according to claim 9, 1-(5,6-dihydro-p-dithiin-2,3-dicarboximido)-N,N-dimethylcyclohexanecarboxamide.

17. A compound according to claim 9, 1-(5,6-dihydro-4H-thiapyran-2,3-dicarboximido)cyclohexanecarboxamide.

18. A method for regulating the growth of plants comprising, applying to the foliage, roots, stems, seeds seed pieces or to soil in which the plants are grown, an effective plant growth regulating amount of a compound of the formula:

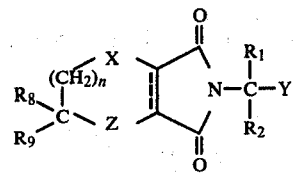

wherein

X is $CH_2$ or S;

Z is S, O, or SO, provided that when Z is O, X cannot be S;

Y is $COOR_3$, —$CONR_4R_5$, —CONHOH, —$CONHNR_6R_7$, —$CONHN^{\oplus}R_6R_7R_7 \cdot halide^{\ominus}$, or CN; n is 0 or 1;

$R_1$ and $R_2$ each represent alkyl $C_1$-$C_4$, or when taken together with the carbon to which they are attached form cycloalkyl $C_4$-$C_8$ or methyl-substituted cycloalkyl $C_4$-$C_9$;

$R_3$ is alkyl $C_1$-$C_4$;

$R_4$ and $R_5$ each represent hydrogen, alkyl $C_1$-$C_4$, phenyl, monohalophenyl, monoalkyl($C_1$-$C_4$)phenyl, or monoalkoxy($C_1$-$C_4$)phenyl;

$R_6$ and $R_7$ are alkyl $C_1$-$C_2$;

$R_8$ is hydrogen, alkyl $C_1$-$C_4$, phenyl, monohalophenyl, monoalkyl($C_1$-$C_4$)phenyl, monoalkoxy($C_1$-$C_4$)phenyl or trifluoromethylphenyl;

$R_9$ is hydrogen or alkyl $C_1$-$C_4$;

and  represents a single or double bond.

19. A method according to claim 18, wherein the active compound is applied to the seeds, seed pieces or soil containing seeds or seed pieces of the plants for which plant growth regulation is desired.

20. A method according to claim 18, wherein the compound is applied to the foliage and stems of the plants for which plant growth regulation is desired.

21. A method according to claim 18, wherein the compound is applied to the roots of the plants for which plant growth regulation is desired.

22. A method according to claim 20, wherein the active compound is applied at the rate of from 0.06 pound to 32 pounds per acre.

23. A method according to claim 18, wherein the compound is of the formula

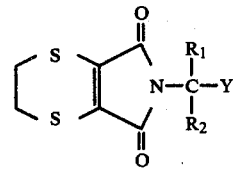

wherein

Y is $COOR_3$, —$CONR_4R_5$, —$CONHNR_6R_7 halide^{\oplus}$ or CN;

$R_1$ and $R_2$ each represent alkyl $C_1$-$C_4$ or when taken together with the carbon to which they are attached form cycloalkyl $C_4$-$C_8$;

$R_3$ is alkyl $C_1$-$C_4$ and $R_4$ and $R_5$ each represent hydrogen or alkyl $C_1$-$C_4$;

$R_6$ and $R_7$ are alkyl $C_1$-$C_2$, either the same or different.

24. A method according to claim 18, wherein X and Z of the formula are each sulfur.

25. A method according to claim 18, wherein X of the formula is $CH_2$ and Z is oxygen.

26. A method according to claim 18, wherein X of the formula is CH$_2$ and Z is sulfur.

27. A method according to claim 18, wherein X of the formula is sulfur and Z is SO.

28. A method according to claim 24, wherein Y of the formula is —CONR$_4$R$_5$.

29. A method according to claim 24, wherein Y of the formula is —CONHNR$_6$R$_7$.

30. A compound according to claim 2, 1-(5,6-dihydro-p-dithiin-2,3-dicarboximido)cyclohexanecarboxylic acid, 2,2-dimethylhydrazide.

31. A method according to claim 28, wherein the compound applied is 1-(5,6-dihydro-p-dithiin-2,3-dicarboximido)cyclohexanecarboxamide; 1-(5,6-dihydro-p-dithiin-2,3-dicarboxamido)cyclopentanecarboxamide; or 1-(5,6-dihydro-p-dithiin-2,3-dicarboximide)-N,N-dimethylcyclohexanecarboxamide.

32. A method according to claim 18, wherein said treated plants are agronomic crops and said treatment produces increase crop yields.

33. A method according to claim 18, wherein said treated plants are agronomic crops planted as seed crops and said treatment accelerates flowering and bolting.

34. A method according to claim 18, wherein said treated plants are leaf crops and said treatment increases leaf size.

35. A method according to claim 18, wherein said treated plants are tuberous plants or root crops and said treatment increases root set and/or root size and weight.

36. A method according to claim 32 wherein the compound is 1-(5,6-dihydro-p-dithiin-2,3-dicarboximido)cyclohexanecarboxylic acid, 2,2-dimethylhydrazide.

37. A method according to claim 32 wherein the compound is N-(1-cyanocyclohexyl)-5,6-dihydro-p-dithiin-2,3-dicarboximide.

38. A compound according to claim 1, 1-(5,6-dihydro-p-dithiin-2,3-dicarboximido)-N-methoxy-cyclohexanecarboxamide.

39. A method according to claim 32 wherein the compound is 1-(5,6-dihydro-p-dithiin-2,3-dicarboximido)-3-methyl, trans (CH$_3$ to CONH$_2$)-cyclohexanecarboxamide.

40. A compound according to claim 1, 2'-chloro-1-(5,6-dihydro-p-dithiin-2,3-dicarboximido)cyclohexanecarboxanilide.

41. A compound according to claim 2, 1-(5,6-dihydro-p-dithiin-2,3-dicarboximido)-N-methyl-cyclohexanecarboxamide.

42. A method according to claim 32 wherein the compound is 2'-chloro-1-(5,6-dihydro-p-dithiin-2,3-dicarboximido)-cyclohexanecarboxanilide.

43. A method according to claim 32 wherein the compound is 1-(5,6-dihydro-p-dithiin-2,3-dicarboximido)-N-methyl-cyclohexanecarboxamide.

44. A compound according to claim 1, 1-(5,6-dihydro-p-dithiin-2,3-dicarboximido)-3-methyl-, trans (CH$_3$ to CONH$_2$)-cyclohexanecarboxamide.

45. A method according to claim 32 wherein the compound is 1-(5,6-dihydro-p-dithiin-2,3-dicarboximido)cyclohexanecarboxamide.

46. A method according to claim 32 wherein the compound is 1-(5,6-dihydro-p-dithiin-2,3-dicarboximido)cyclopentanecarboxamide.

47. A method according to claim 32 wherein the compound is 1-(5,6-dihydro-p-dithiin-2,3-dicarboximido)-N,N-dimethylcyclohexanecarboxamide.

48. A method according to claim 32 wherein the compound is 1-(5,6-dihydro-4H-thiapyran-2,3-dicarboximido)cyclohexanecarboxamide.

49. A method according to claim 32 wherein the compound is 1-(5,6-dihydro-p-dithiin-2,3-dicarboximido)-N-methoxy-cyclohexanecarboxamide.

* * * * *

UNITED STATES PATENT OFFICE
CERTIFICATE OF CORRECTION

Patent No. 4,164,404     Dated August 14, 1979

Inventor(s) MARINUS LOS and BRYANT LEONIDAS WALWORTH

It is certified that error appears in the above-identified patent and that said Letters Patent are hereby corrected as shown below:

Claim 18, Column 34, Line 26 after "is" and before "hydrogen" insert -- mononitrophenyl, --

Signed and Sealed this

Thirteenth Day of November 1979

[SEAL]

Attest:

RUTH C. MASON
Attesting Officer

LUTRELLE F. PARKER
Acting Commissioner of Patents and Trademarks